United States Patent
Kimura et al.

(10) Patent No.: US 6,784,284 B2
(45) Date of Patent: Aug. 31, 2004

(54) SECRETORY MEMBRANE PROTEIN THAT INDUCES OSTEOBLAST DIFFERENTIATION

(76) Inventors: Naoki Kimura, c/o Chugai Research Institute for Molecular Medicine, Inc., 153-2, Nagai, Niihari-mura, Niihari-gun, Ibaraki 300-4101 (JP); Tomoko Toyoshima, c/o Chugai Research Institute for Molecular Medicine, Inc., 153-2, Nagai, Niihari-mura, Niihari-gun, Ibaraki 300-4101 (JP)

(*) Notice: Subject to any disclaimer, the term of this patent is extended or adjusted under 35 U.S.C. 154(b) by 0 days.

(21) Appl. No.: 09/855,266

(22) Filed: May 14, 2001

(65) Prior Publication Data

US 2002/0128435 A1 Sep. 12, 2002

Related U.S. Application Data

(60) Division of application No. 09/441,722, filed on Oct. 1, 1999, now Pat. No. 6,271,366, which is a continuation-in-part of application No. PCT/JP98/01511, filed on Apr. 1, 1998.

(30) Foreign Application Priority Data

Apr. 1, 1997 (JP) .............................. 9-99653

(51) Int. Cl.⁷ ..................... C07K 14/00; C07K 14/525; G01N 33/53
(52) U.S. Cl. ..................... 530/350; 530/351; 435/7.1; 435/7.2
(58) Field of Search .................. 530/350, 351; 536/23.1, 23.5, 23.52; 435/69.1, 70.1, 7.1, 7.2

(56) References Cited

PUBLICATIONS

Ngo et al., 1994, Computational Complexity, Protein Structure prediction, and the Levinthal Paradox, The Protein Folding Problem and Tertiary Structure Prediction, pp. 492–495.*

Wells, Aditivity of Mutational Effects in Proteins, 1990, Biochemistry, vol. 26, No:37, pp. 8509–8517.*

* cited by examiner

*Primary Examiner*—Lorraine Spector
*Assistant Examiner*—Jegatheesan Seharaseyon

(57) ABSTRACT

Three genes encoding secretory membrane proteins have been successfully isolated from an osteoblast-like cell line by a method for specifically cloning secretory membrane proteins. One of these genes encodes a novel receptor protein. The protein has only the extracellular region, binds to the cell membrane via a GPI anchor, and carries therein a cysteine-rich, repetitive region commonly conserved in the TNF receptor super family. Overexpression of this protein in osteoblast-like cell line cells suppresses cell proliferation, changes cell morphology, and increases alkaline phosphatase activity, which is one of markers for differentiation of osteoblasts.

27 Claims, 9 Drawing Sheets

| | | |
|---|---|---|
| 1 | AGCTCACAGCC | 11 |
| 12 | ATGGTTACCTTCAGCCACGTCTCCAGTCTGAGTCACTGGTTCCTCTTGCTGCTGCTGCTG | 71 |
| 1 | <u>M  V  T  F  S  H  V  S  S  L  S  H  W  F  L  L  L  L  L  L</u> | 20 |
| 72 | AATCTGTTCTTGCCGGTAATATTTGCTATGCCTGAATCATACTCCTTCAACTGTCCCGAT | 131 |
| 21 | <u>N  L  F  L  P  V  I</u>  A  M  P  E  S  Y  S  F  N  C  P  D | 40 |
| 132 | GGTGAATACCAGTCTAATGATGTCTGTTGCAAGACCTGTCCCTCAGGTACATTTGTCAAG | 191 |
| 41 | G  E  Y  Q  S  N  D  V  C  C  K  T  C  P  S  G  T  F  V  K | 60 |
| 192 | GCGCCCTGCAAAATCCCCCATACTCAAGGACAATGTGAGAAGTGTCACCCAGGAACATTC | 251 |
| 61 | A  P  C  K  I  P  H  T  Q  G  Q  C  E  K  C  H  P  G  T  F | 80 |
| 252 | ACAGGGAAAGATAATGGCCTGCATGATTGTGAACTTTGCTCCACCTGTGATAAAGACCAG | 311 |
| 81 | T  G  K  D  N  G  L  H  D  C  E  L  C  S  T  C  D  K  D  Q | 100 |
| 312 | AATATGGTGGCTGACTGTTCTGCCACCAGTGACCGGAAATGCGAGTGCCAAATAGGTCTT | 371 |
| 101 | N  M  V  A  D  C  S  A  T  S  D  R  K  C  E  C  Q  I  G  L | 120 |
| 372 | TACTACTATGACCCAAAATTTCCGGAATCATGCCGCCCATGTACCAAGTGTCCCCAAGGA | 431 |
| 121 | Y  Y  Y  D  P  K  F  P  E  S  C  R  P  C  T  K  C  P  Q  G | 140 |
| 432 | ATCCCTGTCCTCCAGGAATGCAACTCCACAGCTAACACTGTGTGCAGTTCATCTGTTTCA | 491 |
| 141 | I  P  V  L  Q  E  C  N  S  T  A  N  T  V  C  <u>S  S  S  V  S</u> | 160 |
| 492 | AATCCCAGAAACTGGCTGTTCCTACTGATGCTAATTGTCTTCTGTATCTGA | 542 |
| 161 | <u>N  P  R  N  W  L  F  L  L  M  L  I  V  F  C  I</u>  * | 177 |
| 543 | AGAAGATAAAGGTTCTACAGATGGTGTCTGTAGCTTCCTTTTATTGCTGTGAAGAGAA | 600 |
| 601 | ACCATGGAGGCAACTCTTTCATTTTATTTTATTTTTTAATGTCTTGAACTTGATTTGAAG | 660 |
| 661 | ACCAGGCTGGACTCAAACTCACAGAGATCCGGACTAGGCACCTCTAATATAGGAAAACAT | 720 |
| 721 | TGAATTGGGACTGGCTTACAGTTTCAGAAGTTCTGTCCATGATTATCATAGTGCGAAGCA | 780 |
| 781 | TGGAGGCACGGAGGCACACATGGTGCTGGAGAAGAAGCTGAGAGTTCTGCATCTTGATCT | 840 |
| 841 | GCAAGCAATAAAAGGAGACTGTGTGCCACACTACACATAGCTTGAACATAGGAGACCTCA | 900 |
| 901 | AAGCCTGTCCCCACAGTGACAAACTTCCTCCAACAAGGTCATACCTCCTAATAATACCAT | 960 |
| 961 | TTCTTATGAGGCAAGCATTCAAACACATGAGTCTATGAGGGCCAAACCAATTCAAACCAC | 1020 |
| 1021 | CACAGGTTAACAATTGCCCTCTGCAGCTCTCTGGTGGAGGCCCTCCTTGAGAGTAAGTAA | 1080 |
| 1081 | CAATTTAGATGAAGGCAAGTCCTGGTATCAGGTCCAAAAGAAACTCAGGATGAATGGTCC | 1140 |
| 1141 | ACTGTGGTTCCTATTAACATACTGAAGAACATGACCTCACCTTAGACTTCTCCACCTCAC | 1200 |
| 1201 | TGGCTTCCCTTCCCCTAGCTTCTCATTCCCAGGTAACCCTGCCATTTTTTGGTAATGTGC | 1260 |
| 1261 | CTTCTTGGTTCTTCCTCTCCTTTCCCCCTCTCTTCTGGTCCTTATTTCTCTTCCTCTCCC | 1320 |
| 1321 | ACTCTCCACCAGCCGCCTCTTAAGGCCTGAGTCAGTCTGCAGGCCATGTTTAATCTACTA | 1380 |
| 1381 | CTTTCTCTCTGCTCTGGACTCATCCAGATGTCTCTGGCTGAGCTCTCCCTCCTATCTACA | 1440 |
| 1441 | ATAAAACCTTCCCCCTAACCAGAAATGGAACAGTTTTGTCCTCACTTTGTACATCTGGTG | 1500 |
| 1501 | CCTGAAACC | 1509 |

FIG. 1

```
7F4     CPDGEY---QSNDVC CKTCPSGTFVKAPCK IPHTQGQCEKCHPGT FTGKDNGLHDCELCS 60
mTNFR   CPGGKYVHSKNNSIC CTKCHKGTYLVSDCP SPGRDTVCRECEKGT FTASQNYLRQCLSCK 60

7F4     TCDKD--QNMVADCS ATSDRKCEC---QIG LYYYDPKFPESCRPC TKCPQGIPVLQECNS 120
mTNFR   TCRKEMSQVEISPCQ ADKDTVCGCKENQFQ RYLSETHFQ--CVDC SPCFNGTVTIP-CKE 120

7F4     TANTVC                                                          126
mTNFR   TQNTVC                                                          126
```

FIG. 2

SECRETORY MEMBRANE PROTEIN THAT INDUCES OSTEOBLAST DIFFERENTIATION

This application is a divisional of U.S. patent application Ser. No. 09/441,722, now U.S. Pat. No. 6,271,366, filed Oct. 1, 1999, which is a continuation-in-part of PCT/JP98/01511 filed Apr. 1, 1998, and claims priority from Japanese Application No. 9/99653 filed Apr. 1, 1997.

TECHNICAL FIELD

The present invention relates to a novel secretory membrane protein involved in differentiation of osteocytes, a DNA encoding said protein, a vector comprising said DNA, a host cell carrying said vector, an antibody against said protein, a method for screening a compound using said protein, and a compound obtainable by said screening method.

BACKGROUND ART

Regeneration of bones by the action of osteoblasts, bone formation, is an important phenomenon in vertebrates for maintaining a living body. Factors involved in bone formation include hormones such as estrogen, calcitonin, and parathyroid hormone (PTH); growth factors such as bone morphologenic protein (BMP); and chemicals such as active vitamin D, calcium preparations, and vitamin K2. Estrogen, calcitonin, active vitamin D, and calcium preparations are used as medicine for controlling bone mass in osteoporosis or similar cases. Any of these drugs can be used to prevent decreases of bone mass by inhibiting bone resorption, rather than for increasing bone mass. An effective remedy for enhancing bone formation has thus not been developed yet.

BMP, which is expected to be a new medicine for treating bone disorders, is a unique cytokine that functions as an ectopic formation signal. BMP is thought to effectively form bone (cartilaginous ossification) by replacing cartilaginous callus with new bone cells in repairing fractures or bone deficits (Duprez D. M., Coltey M., Amthor H., Brickell P. M., Tickle, C. (1996) Dev. Biol. 174, 448–452, Bone morphogenetic protein-2 (BMP-2) inhibits muscle development and promotes cartilage formation in chick limb bud cultures; Nakase, T., Nomura, S., Yoshikawa, H., Hashimoto, J., Hirota, S., Kitamura, Y., Oikawa, S., Ono, K., Takaoka, K. (1994) J. Bone Miner. Res. 9, 651–659, Transient and localized expression of bone morphogenetic protein 4 messenger RNA during fracture healing).

There is no conclusive evidence to show that BMP is involved in bone formation caused in conjunction with bone resorption during constant bone formation. Therefore, it is doubtful that BMP can be used as a medicine to promote bone formation by activating and promoting differentiation of osteoblasts that are essential for constant bone formation. Factors involved in constant bone formation have not been reported yet.

SUMMARY OF THE INVENTION

An objective of the present invention is to provide a novel protein involved in constant bone formation and a gene encoding it. Another objective of the invention is to provide a vector in which the gene is inserted, a host cell carrying the vector, and an antibody that binds to the protein. Still another objective of this invention is to provide a method for screening a compound that binds to the protein, such as a ligand, using the protein.

The present inventors investigated how best to achieve the above objectives and succeeded in isolating three types of genes each encoding secretory membrane proteins from an osteoblast-like cell line by specifically cloning genes encoding secretory membrane proteins. The analysis of one of the isolated genes revealed that a protein encoded by the gene is a novel receptor protein with only the extracellular region, which binds to the plasma membrane through a GPI anchor, and contains cysteine-rich, repetitive regions conserved in TNF receptor super family molecules. Furthermore, the inventors found that high-level expression of the protein in the osteoblast-like cell line inhibited cell proliferation, altered the cells morphologically, and enhanced alkaline phosphatase activity that is one of indicators of the differentiation of osteoblasts. Based on this finding that the isolated protein is involved in the differentiation of osteocytes, the inventors also found that a drug candidate compound for treating bone disorders can be screened using the protein.

The present invention relates to novel secretory membrane proteins, genes encoding them, and a method for screening a drug candidate compound using the proteins. More specifically, the invention relates to:

(1) a protein comprising the amino acid sequence of SEQ ID NO:1 or 2, or the same sequence in which one or more amino acids are replaced, deleted, or added, and having activity to induce differentiation of osteocytes;

(2) a protein encoded by a DNA hybridizing the DNA comprising the nucleic acid sequence of SEQ ID NO:3, and having activity to induce differentiation of osteocytes;

(3) a DNA encoding the protein of SEQ ID NO:1 or 2;

(4) a vector in which the DNA of (3) is inserted;

(5) a host cell carrying the vector of (4);

(6) an antibody binding to the protein of (1) or (2);

(7) a method for screening a compound that binds to the protein of (1) or (2), wherein said method comprises the steps of
 (a) bringing a test compound into contact with the protein of (1) or (2), and
 (b) screening a compound that binds to the protein of (1) or (2);

(8) a method for screening a compound that promotes or inhibits the osteocyte differentiation-inducing activity of the protein of (1) or (2), wherein said method comprises the steps of
 (a) bringing a test compound into contact with the protein of (1) or (2) expressed on the cell surface,
 (b) detecting the osteocyte differentiation inducing activity of the protein of (1) or (2), and
 (c) screening a compound that promotes or inhibits the osteocyte differentiation inducing activity of the protein of (1) or (2), in comparison with the assay in the absence of the test compound;

(9) a compound that binds to the protein of (1) or (2), wherein said protein is obtainable by the method of (7);

(10) a compound that promotes or inhibits the osteocyte differentiation inducing activity of the protein of (1) or (2), wherein said protein is obtainable by the method of (8);

(11) the compound of (9) or (10), wherein said compound is naturally occurring;

(12) the compound of (9) or (10), wherein said compound is a ligand;

(13) the compound of (9) or (10), wherein said compound is an agonist; and

(14) the compound of (9) or (10), wherein said compound is an antagonist.

The invention also includes a substantially pure polypeptide (1) having an amino acid sequence at least 70% (e.g., at least 70, 80, 90, 95, or 99%) identical to SEQ ID NO:2, (2) having an amino acid sequence that is SEQ ID NO:2 containing at least one conservative amino acid substitution (preferably between 1–30, and more preferably 15 or fewer (e.g., 5 or fewer or even 3 or fewer) substitutions, or (3) encoded by a first nucleic acid that hybridizes under stringent conditions to a second nucleic acid consisting of SEQ ID NO:3. The polypeptide can induce differentiation of an osteocyte (e.g., a human osteocyte).

Also featured in the invention is an isolated nucleic acid encoding a polypeptide of the invention. In addition, nucleic acid fragments that hybridize under stringent conditions to SEQ ID NO:3, such as hybridization probes and PCR primers, are also included in the invention.

The invention further features nucleic acid and viral vectors, as well as transformed host cells, containing a nucleic acid of the invention. Also included in the invention is an antibody (e.g., a monoclonal antibody), or a composition of polyclonal antibodies (e.g., an antiserum) that specifically binds to a polypeptide of the invention.

The invention also features a method of screening for a compound that binds to a polypeptide by (1) contacting a compound with a polypeptide of the invention, and (2) determining whether the compound has bound to the polypeptide. Other methods included in the invention include: (1) a method of screening for a compound that induces osteocyte differentiation by contacting a compound with a polypeptide of the invention, and determining whether the ability of the polypeptide to induce osteocyte differentiation in the presence of the compound is greater than in the absence of the compound, such being an indication that the compound induces osteocyte differentiation; and (2) a method of screening for a compound that inhibits osteocyte differentiation by contacting a compound with a polypeptide of the invention, and determining whether the ability of the polypeptide to induce osteocyte differentiation in the presence of the compound is less than in the absence of the compound, and if the ability is less, the compound inhibits osteocyte differentiation.

In addition, the invention includes a compound that specifically binds to a polypeptide of the invention. The compound can be an agonist or antagonist of the polypeptide. If the compound is naturally occurring, the compound can be isolated or purified.

The present invention relates to a novel secretory membrane protein involved in constant bone formation. The nucleotide sequence of mouse-derived cDNA isolated by the present inventors is shown in SEQ ID NO:3; the amino acid sequence of the protein encoded by the cDNA containing a signal peptide, in SEQ ID NO:1; and the amino acid sequence of the mature protein in which the N-terminal signal peptide is deleted, in SEQ ID NO:2. The present inventors designated the isolated clone "7F4." The 7F4 protein, which is one of the proteins of the present invention, contains a cysteine-rich region conserved in the TNF receptor sub family and the hydrophobic region at the N-terminus (signal sequence region) and the C-terminus. No protein having significant homology with the amino acid sequence of 7F4 protein was found in the database. Therefore, the 7F4 protein is assumed to be a novel protein belonging to the TNF receptor super family (Beulter, B., and Huffel, C. V. (1994) SCIENCE 264, 667–668, Unraveling function in the TNF ligand and receptor families) (refer to FIG. 6).

When a transformant of a KUSA cell (which is derived from normal mouse bone marrow stroma, has hematopoiesis indication potential, and causes the bone formation by inducing bone marrow during in vivo bone marrow transplantation (Umezawa, A., Maruyama, T., Segawa, K., Shadduck, R. K., Waheed, A., and Hata, J. (1992) Multipotent marrow stromal cell line is able to induce hematopoiesis in vivo, J. Cell Physiol. 151, 197–205)) and overexpressing 7F4 protein was treated with PI-specific phospholipase C, the quantity of the protein present on the cell surface was lowered (Example 7). This suggested that the 7F4 protein does not exist in the intracellular region and is structurally fixed on the cell surface mediated by a GPI anchor. Known GPI anchor-mediated membrane proteins include, for example, the CNTF receptor. The intracellular regions of IL-6 and IL-11 receptors are extremely short and do not contain the region involved in signal transduction after a ligand binds to the receptor. When these receptors bind to ligands, they associate with gp130 and transmit the signals into the cell using gp130 as a signal transduction chain. Like many cytokine receptors, 7F4 may transmit signals to a nucleus by associating with a signal transduction chain such as gp130. In fact, when the 7F4 protein was overexpressed in KUSA cells, the cell morphology changed in correlation with the expression level; the cell proliferation rate tended to decline (Example 6); and alkaline phosphatase activity, one of the indicators of the differentiation of osteoblasts, increased (Example 8). These facts indicate that the 7F4 protein relates to the differentiation signals of osteocytes. The 7F4 protein and compounds that bind to the protein could be used to treat and prevent bone disorders as described below. Alternatively, 7F4 can be used in diagnosis as a marker for osteocyte differentiation.

It was reported that the expression level of a bone formation marker increased and that the osteoblasts differentiated by themselves when osteoblasts were cultured for a long time (Matsumoto, T., Igarashi, C., Takeuchi, Y., Harada, S., Kikuchi, T., Yamato, H., and Ogata, E. (1991) Stimulation by 1,25-dihydroxyvitamin D3 of in vitro mineralization induced by osteoblast-like MC3T3-E1 cells, Bone 12, 27–32; Sudo, H., Kodama, H. A., Amagai, Y., Yamamoto, S., and Kasai, S. (1983) In vitro differentiation and calcification in a new clonal osteogenic cell line derived from newborn mouse calvaria, J. Cell Biol. 96, 191–198). BMP is known as a unique bone formation factor inducing bone tissues by causing bone formation through cartilage formation. No cartilaginous cells are observed in bone formation in osteoblasts, especially in KUSA cells. This bone differentiation mechanism differs from that of BMP (Wozney, J. M., Rosen, V., Celeste, A. J., Mitsock, L. M., Whitters, M. J., Kriz, R. W., Hewick, R. M., and Wang, E. A. (1988), Novel regulators of bone formation: molecular clones and activities, Science 242, 1528–1534), suggesting the existence of unknown bone formation factors. The 7F4 protein is a potential candidate for a new bone formation factor.

The present invention also relates to the proteins functionally equivalent to 7F4 protein. One method well known in the art for isolating proteins functionally equivalent to the 7F4 protein is to introduce mutagenesis in the proteins. For example, one skilled in the art can prepare proteins functionally equivalent to the 7F4 protein by introducing an appropriate mutation in the amino acid sequence of the 7F4 protein (SEQ ID NO:1 or 2) by site-directed mutagenesis (Hashimoto-Gotoh, T., Mizuno, T., Ogasahara, Y., and Nakagawa, M. (1995), An oligodeoxyribonucleotide-directed dual amber method for site-directed mutagenesis, Gene 152, 271–275; Zoller, M. J. and Smith, M. (1983) Oligo-nucleotide-directed mutagenesis of DNA fragments cloned into M13 vectors, Methods Enzymol. 100, 468–500; Kramer, W., Drutsa, V., Jansen, H. W., Kramer, B., Pflugfelder, M., and Fritz, H. J. (1984). The gapped duplex DNA approach to oligonucleotide-directed mutation construction, Nucleic Acids Res. 12, 9441–9456; Kramer W. and Fritz H. J. (1987) Oligo-nucleotide-directed construction of mutations via gapped duplex DNA Methods. Enzymol. 154, 350–367, Kunkel, T A (1985) Rapid and efficient site-specific mutagenesis without phenotypic selection, Proc. Natl. Acad. Sci. USA. 82, 488–492). Mutation of amino acids could occur in nature, too. The protein of the present invention includes those comprising amino acid sequences of the 7F4 protein in which one or more amino acids are mutated and functionally equivalent to the 7F4 protein. From the functional aspect, amino acids to be mutated are usually 30 residues or less, preferably 15 residues or less, more preferably 5 residues or less, and still preferably, 3 residues or less.

An alternative method known in the art to isolate functionally equivalent proteins is, for example, the method using a hybridization technique (Sambrook, J. et al., Molecular Cloning 2nd ed. 9.47–9.58, Cold Spring Harbor Lab. Press, 1989). One skilled in the art can readily isolate DNA having high homology with a whole or part of the DNA sequence (SEQ ID NO:3) encoding the 7F4 protein, and isolate functionally equivalent proteins to the 7F4 protein from the isolated DNA. The proteins of the present invention include those encoded by DNA that hybridizes with a whole or part of the DNA sequence encoding the 7F4 protein and functionally equivalent to the 7F4 protein. These proteins include a homologue of mammals corresponding to the protein derived from mouse (for example, a protein encoded by a human gene detected by Northern blotting described in Example 3). Generally, the proteins obtained by the hybridization technique show high homology with the 7F4 protein in the amino acid sequence. "High homology" means 40% or more, preferably 60% or more, and more preferably 80% or more homology.

The term "protein functionally equivalent to 7F4 protein" used herein means proteins having the activity to induce differentiation of osteocytes like the 7F4 protein. The term "activity to induce differentiation of osteocytes" used herein means the activity to decrease the cell proliferation rate of osteocytes and alter the morphology of the cells. This activity can be detected by, for example, morphological observation of osteocytes under a microscope and an assay of alkaline phosphatase activity that is usually used as a marker for differentiation of osteocytes (N. C. Partrige, D. Alcorn, V. P. Michelangeli, G. Ryan & T. J. Martin (1983) Cancer Res. 43, 4308–14, Morphological and biochemical characterization of four clonal osteogenic sarcoma cell lines of rat origin; J. K. Burns & W. A. Peck (1978) Science 199, 542–4, Bone cells: a serum-free medium supports proliferation in primary culture). The alkaline phosphatase activity can be measured by disrupting cells by, for example, ultrasonocation to obtain cell extract, incubating the extract with p-nitrophenyl phosphate which is a substrate of alkaline phosphatase, and measuring the quantity of p-nitrophenol produced with a spectrophotometer. Alternatively, the activity can be determined by detecting indicators such as osteocalcine or collagen type I.

The protein of the present invention can be prepared as recombinant proteins or natural proteins by methods known in the art. For example, recombinant proteins can be prepared by expressing a part of the protein of the invention excluding the region necessary for the protein to bind to the membrane, allowing cells to secrete the protein, recovering the culture supernatant of these cells, concentrating the supernatant, and purifying the protein by chromatography utilizing ion exchange, reverse phase, or gel filtration, or by affinity chromatography with a column in which the antibodies against the protein of the present invention are fixed, or by combination thereof. Alternatively, the protein of the invention can be prepared by expressing the protein in host cells (e.g., animal cells or E. coli) as a fusion protein with gultathione S transpherase protein, or a recombinant protein with multiple histidine residues. The expressed protein can be purified using a gultathione column or nickel column. Furthermore, if necessary, regions of the fusion protein excluding the desired protein can be digested and removed with tronbin or factor Xa. The protein of the invention can be isolated in the natural form by, for example, purifying the cell extract containing the protein of the invention with an affinity column to which the antibody of the present invention described below is bound.

The present invention relates to DNA encoding the above-described protein of the invention. Any type of DNA, such as cDNA synthesized from mRNA, genomic DNA or synthetic DNA, can be used as long as DNA encodes the protein of the present invention. The DNA of the present invention can be prepared by constructing a cDNA library from the cells expressing the protein of the invention and conducting hybridization using a part of the DNA sequence of the present invention (for example, DNA shown in SEQ ID NO:3) as a probe. Alternatively, the DNA of the present invention can be obtained by preparing RNA from the cells expressing the protein of the invention, synthesizing oligo-DNAs based on the DNA sequence of the invention (for example, DNA sequence shown in SEQ ID NO:3), and performing PCR using the oligo-DNAs as primers to amplify cDNA encoding the protein of the invention. The DNA of the present invention can be used for producing the protein of the invention as a recombinant protein. When the DNA encoding the protein of the invention is defective, it can be applied to functional inhibition by antisense or gene therapy for replacing the defective gene with a normal one.

The present invention also relates to a vector into which the DNA of the present invention is inserted. The vector of the present invention is not particularly limited. When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug (e.g., ampicillin, tetracycline, kanamycin, or chloramphenicol). For example, M13-series vectors, pUC-series vectors, pBR322, pbluescript, pCR-Script, etc., can be used. PGEM-T, pDIRECT, and pT7 can also be used for subcloning and extracting cDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5, αHB101, or XL1 Blue, are used as a host cell, the vector should have a promoter (e.g., lac, T7) that can efficiently express the desired gene in E. coli. Other examples of the vectors are pGEM, pEGFP, or pET (a host cell is BL21 expressing T7 RNA polymerase).

In order to express the vector in animal cells, such as CHO, COS, or NIH3T3 cells, the vector should have a promoter necessary for expression in such cells (e.g., SV40, MMLV-LTR, EF1α, or CMV promoter) and preferably a marker gene for selecting transformants (for example, a drug resistance gene selected by a drug (e.g., neomycin, G418)). Examples of the vectors with these characteristics include pMAM, pDR2, pBK-RSV, pBK-CMV, pOPRSV, and pOp13.

As a host-vector system for amplifying the copy number in cells, CHO cells deficient in nucleic acid synthetic pathways are used as a host, and a vector (such as PCHOI) with a DHFR gene that compensates for the deficiency is inserted in the cells. The vector can be amplified using methotrexate (MTX). For temporary expression, COS cells which have SV40 T antigen on the chromosomes can be transformed with a vector (such as pcD) having SV40 replication origin.

The DNA of the invention can be expressed in animals by, for example, inserting the DNA of the invention into an appropriate vector and introducing the vector into a living body by the retrovirus method, liposome method, cationic liposome method, or adenovirus method. Any vector can be used without limitation. pAdexLcw or pZLPneo is preferably used. General genetic manipulation, such as insertion of the DNA of the invention into a vector, can be performed by conventional methods (Molecular Cloning, 5.61–5.63).

The present invention relates to a host cell into which the vector of the present invention has been introduced. The host cell into which the vector of the invention is introduced is not particularly limited. E. coli or various animal cells can be used. Examples of E. coli are JM109, DH5α, and HB101; examples of animal cells are CHO cells, COS cells, 3T3 cells, and Hela cells. CHO cells are particularly preferable for high-level expression.

Various cells can be used for in vivo expression of the DNA of the invention without limitation. For gene therapy of bone disorders, cells such as mesenchymal cells or osteoblasts collected from a living body are suitably used as target cells.

The vector can be introduced into the host cell by the calcium phosphate method, the DEAE-dextran method, electroporation, or lipofection.

The present invention relates to an antibody that binds to the protein of the invention. The antibody of the invention can be used in any form, such as monoclonal or polyclonal antibodies, and includes antiserum obtained by immunizing a rabbit with the protein of the invention, all classes of polyclonal and monoclonal antibodies, human antibodies, and humanized antibodies produced by genetic recombination. For example, the antibody of the present invention can be prepared as follows. Polyclonal antibodies can be prepared by immunizing small animals such as rabbits with the protein of the invention to obtain serum, obtaining the fraction exclusively recognizing the protein of the invention using an affinity column coupled with the protein of the invention, and purifying immunoglobulin G or M from the fraction using a protein A or protein G column. Monoclonal antibodies can be prepared by immunizing small animals such as mice with the protein of the invention, excising the spleen from the animal, homogenizing the organ into cells, fusing the cells with mouse myeloma cells using a reagent such as polyethylene glycol, selecting clones that produce antibodies against the protein of the invention from the fused cells (hybridomas), transplanting the obtained hybridoma into the abdominal cavity of a mouse, and extracting ascites from the mouse. The obtained monoclonal antibodies can be purified by, for example, ammonium sulfate precipitation or by column chromatography using a protein A or protein G column, a DEAE ion exchange column, or an affinity column to which the protein of the invention is coupled. The antibody of the invention can be used for purifying and detecting the protein of the invention. It can also be used for antibody therapy of bone disorders. In antibody therapy, human antibodies or humanized antibodies are preferred to minimize immunogenicity.

The present invention relates to a method for screening a compound that binds to the protein of the invention and to a compound (such as a ligand, an agonist, or an antagonist) obtainable by this screening method.

One embodiment of the screening method comprises the steps of (a) bringing a test sample into contact with the protein of the invention and (b) selecting a compound that binds to the protein of the invention. Any sample can be used for this screening method without limitation. Examples are cell extract, culture supernatant, proteins, peptides, or synthetic low molecular compounds. The protein of the invention can be, for example, a purified protein, the expressed form on the cell membrane, or a cell membrane fraction. Such a protein can be contacted with a test sample. The binding activity of the sample to the protein of the invention can be determined by, for example, methods known in the art as described below.

Another embodiment comprises the steps of (a) bringing a test sample into contact with the protein of the invention expressed on the cell surface, (b) detecting osteocyte differentiation inducing activity of the protein of the invention, and (c) selecting a compound promoting or inhibiting osteocyte differentiation inducing activity of the protein of the invention in comparison with the activity detected in the absence of a test sample. Cells which do not produce a ligand binding to the protein of the invention are preferably used as the cells for expressing the protein of the invention. The protein of the invention can be expressed on the cell surface by, for example, inserting the DNA encoding the protein of the invention into an appropriate vector and inserting the vector into a cell. The osteocyte differentiation inducing activity of the protein of the invention can be measured by morphological observation of osteocytes under a microscope or assay of alkaline phosphatase activity, which is generally used as an osteocyte differentiation marker (N. C. Partrige, D. Alcorn, V. P. Michelangeli, G. Ryan & T. J. Martin (1989) Cancer Res. 43, 4308–14, Morphological and biochemical characterization of four clonal osteogenic sarcoma cell lines of rat origin; J. K. Burns & W. A. Peck (1978) Science 199, 542–4, Bone cells; a serum-free medium supports proliferation in primary culture). The alkaline phosphatase activity can be determined by, for example, disrupting cells by ultrasonication, obtaining cell extract, incubating the extract with p-nitrophenol phosphate which is a substrate of alkaline phosphatase, and determining the quantity of p-nitrophenol produced with a spectrophotometer. The activity can also be measured using Osteocalcine or collagen type I as an indicator.

Specifically, the screening method can be performed as described below. A ligand to the protein of the invention can be isolated using the protein by preparing a cDNA library in phage vectors (such as λgt11 and ZAP) from the cells, which is predicted to express ligands (e.g., osteoblast cell lines such as KUSA, ROS17/2.8, UMR106-01, UMR106-06, MC3T3E1, HOS-TE85, MG63, SaOS2, UMR206, RCT1, and C3H10T1/2, or fibroblast cell lines such as OP9, stroma cells, and NIH3T3), expressing the cDNA library on LB-agarose, fixing the expressed proteins on the filter, and purifying the protein of the invention labeled with biotin or fused with GST protein. The purified protein is then reacted with the above-described filter, and plaques expressing the protein binding to the filter are detected using streptavidin or anti-GST antibody by the West Western blotting method (Skolnik, E. Y., Margolis, B., Mohammadi, M., Lowenstein, E., Fischer, R., Drepps, A., Ullrich, A., and Schlessinger, J. (1991) Cloning of PI3 kinase-associated p85 utilizing a novel method for expression/cloning of target proteins for receptor tyrosine kinases. Cell 65, 83–90). The ligands of the present invention can also be prepared by the two hybrid system ("MATCHMAKER Two-Hybrid System" (Clontech), "Mammalian MATCHMAKER Two-Hybrid Assay Kit" (Clontech), "MATCHMAKER One-Hybrid System" (Clontech), or "HybriZAP Two-Hybrid Vector System" (Stratagene). References: "Dalton, S. and Treisman, R. (1992) Characterization of SAP-1, a protein recruited by serum response factor to the c-fos serum response element. Cell 68, 597–612"). Namely, the protein of the invention is fused to the SRF binding region or GAL4 binding region and the fused protein is expressed in yeast cells. A cDNA library is prepared from cells predicted to express a ligand so as to express the ligand fused to the VP16 or GAL4 transcriptional activation region. The above cDNA library is introduced into the above yeast cells. cDNA derived from the library is isolated from positive clones, introduced in E. coli cells, and expressed in the cells (when a protein that binds to the protein of the present invention is expressed in yeast cells, the binding of the two proteins activates the reporter gene to thereby detect positive clones). Alternatively, the ligand of the invention can be prepared by the direct expression cloning method (Yokota, T., Otsuka, T., Mosmann, T., Banchereau, J, DeFrance, T., Blanchard, D., De Vries, J. E., Lee, F., and Arai, K. (1986) Isolation and characterization of a human interleukin cDNA clone, homologous to mouse B-cell stimulatory factor 1, that expresses B-cell- and T-cell-stimulating activities, Proc. Natl. Acad. Sci. USA 83, 5894–5898). Namely, the protein of the invention is expressed in cells in which no corresponding ligand is expressed. An expression cDNA library is constructed from cells that are predicted to express a ligand and introduced into cells such as COS to obtain a culture supernatant. The resulting supernatant is added to the above-described cells expressing the protein of the invention, and the ligand is detected by using some changes of the cells as an indicator (e.g., proliferation rate, cell morphology, expression of alkaline phosphatase, etc.). The ligand of the invention can also be prepared by applying the culture supernatant of cells that is expected to express the ligand of the invention to an affinity column in which the protein of the invention is fixed to purify the protein that specifically binds to the column. DNA encoding the ligand can be prepared by analyzing the amino acid sequence of the obtained protein (ligand), synthesizing oligo DNA based on the sequence, and screening a cDNA library using the oligo DNA as a probe. The term "ligand" used herein means a protein, which binds to the protein of the present invention expressed on the cell membrane to activate its function.

Using the protein of the present invention, an agonist and an antagonist to the protein of the invention can be isolated by methods well known in the art, for example, by the method in which compounds, natural substance banks, or a random phase peptide display library is contacted with the immobilized protein of the invention and the binding molecules are screened, or by the screening method using high-throughput based on combinatorial chemistry techniques (Wrighton, N. C., Farrell, F. X., Chang R., Kashyap A. K., Barbone F. P., Mulcahy L. S., Johnson D. L., Barrett R. W., Jolliffe L. K., and Dower W. J., Small peptides as potent mimetics of the protein hormone erythropoietin, Science (UNITED STATES), Jul. 26, 1996, 273 p458–64; Verdine G. L., The combinatorial chemistry of nature, Nature (ENGLAND), Nov. 7, 1996, 384, p11–13; Hogan J. C. Jr., Directed combinatorial chemistry, Nature (ENGLAND) Nov. 7, 1996, 384, p17–9). The term "agonist" used herein means a molecule that produces similar phenomena to those produced by the binding of the protein of the invention to the ligand of the invention (activation of the protein of the invention) and that can specifically bind to the protein of the invention. The term "antagonist" means a molecule that specifically binds to the protein of the invention to inhibit its function.

Isolated ligands, agonists, and antagonists can be used as follows. Ligands, agonists, or antagonists may be administered to induce proliferation and activation of osteoblasts, thereby increasing the quantity of bones and promoting bone formation in osteoporosis or osteoarthropathy associated with aging. These substances can also be used in anti-cancer therapy based on their regulatory function of osteocyte differentiation in osteosarcoma.

An "isolated nucleic acid" is a nucleic acid which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are mixtures of DNA molecules, vectors, or clones as they occur in a DNA library such as a cDNA or genomic DNA library. Also excluded are RNA molecules that consist of naturally-occurring sequences (e.g., naturally-occurring mRNA), except where the RNA is in a purified state such that it is at least 90% free of other naturally-occurring RNA species. Thus, a naturally-occurring mRNA in a whole mRNA preparation prepared from a cell would not be an "isolated nucleic acid," but a single mRNA species purified to 90% homogeneity from that whole mRNA preparation would be.

The term "substantially pure" as used herein in reference to a given polypeptide means that the polypeptide is substantially free from other biological compounds, such as those in cellular material, viral material, or culture medium, with which the polypeptide may have been associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which the amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent identity" of two amino acid sequences or of two nucleic acids is determined using the algorithm of Karlin and Altschul (Proc. Natl. Acad. Sci. USA 87:2264–2268, 1990), modified as in Karlin and Altschul (*Proc. Natl. Acad. Sci. USA* 90:5873–5877, 1993). Such an algorithm is incorporated into the NBLAST and XBLAST programs of Altschul et al. (*J. Mol. Biol.* 215:403–410, 1990. BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to a reference polypeptide (e.g., SEQ ID NO:2). To obtain gapped alignments for comparison purposes, Gapped BLAST is utilized as described in Altschul et al. (*Nucleic Acids Res.* 25:3389–3402, 1997). When utilizing BLAST and Gapped BLAST programs, the default parameters of the respective programs (e.g., XBLAST and NBLAST) are used. See http://www.ncbi.nlm.nih.gov.

By "hybridizes under stringent conditions" is meant specific and non-covalent equilibrium binding by base-pairing to an immobilized reference nucleic acid in a hybridization solution containing 0.2× SSC (1.75 g/l NaCl, 0.88 g/l Na$_3$citrate 2H$_2$O; pH 7.0) and 0.1 (w/v) sodium dodecyl-sulfate at 68° C. Washings, if any are required to achieve equilibrium, are carried out with the hybridization solution.

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

BRIEF DESCRIPTION OF THE DRAWINGS

FIG. 1 shows the cDNA sequence comprising the open reading frame of clone 7F4 and its amino acid sequence. The upper portion is the nucleotide sequence, and the lower is the amino acid sequence. Two hydrophobic regions are underlined. Presumably, the N-terminus contains the signal sequence, and the C-terminus contains the region that is substituted by the GPI linker.

FIG. 2 compares the amino acid sequence of the extracellular region of 7F4 (upper) and that of mouse TNFR (lower). The boxed letter indicates the consensus cysteine residues, and the other consensus amino acid residues are underlined.

BEST MODE FOR IMPLEMENTING THE INVENTION

Figure 3:
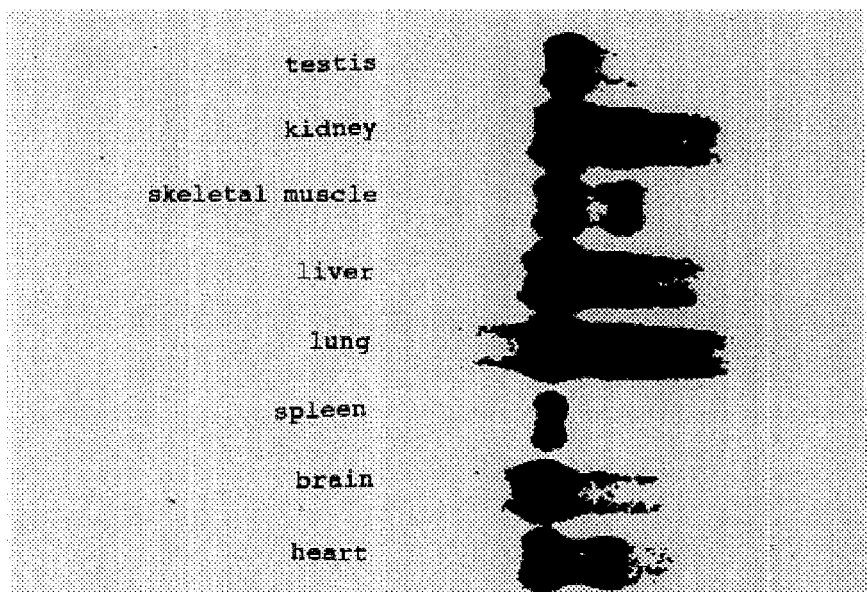
FIG. 3 shows the electrophoretic pattern of the 7F4 gene expression in various mouse tissues analyzed by Northern blotting.

The present invention will be explained in detail below with reference to examples, but is not to be construed to be limited thereto.

EXAMPLE 1

Cloning of 7F4 Genes

A gene encoding the secretory membrane protein which is expressed in mouse osteoblasts KUSA was cloned basically following the signal sequence trap (SST) method. First, pSRαTac, to be used as a vector for expressing a library, was constructed as follows. Plasmid pKCR.Tac-2A (purchased from RIKEN gene bank), in which a full-length human IL-2 receptor gene is inserted, was digested with EcoRI and Eco47III to obtain the gene fragments coding the full-length Tac. The SacI site was deleted from the expression vector for animal cells, pcD-SRα-EF (Takebe, Y., Seiki, M., Fujisawa, J., Hoy, P., Yokota, K., Arai, K., Yoshida, M., Arai, N., Mol. Cell Biol. 8:466–472 (1988), SR alpha promoter: an efficient and versatile mammalian cDNA expression system composed of the simian virus 40 early promoter and the R-U5 segment of human T-cell leukemia virus type 1 long terminal repeat), and the resulting plasmid was digested with EcoRI. The above gene fragment encoding full-length Tac was inserted into the above plasmid to construct pSRαTac. (The Tac signal sequence region can be deleted in this plasmid by digesting with EcoRI and Sac I.) To prepare a 5' enriched cDNA library, the first cDNA strand was synthesized from 5 μg of mRNA prepared from KUSA cells using random primers. The second strand was synthesized using primer 5'-GCGGCCGCGAATTCTGACTAACTGAC-(dG)17 (SEQ ID NO:4) having the EcoRI site, and Taq DNA polymerase after the 5'-terminus of the primer was dc-tailed with terminal nucleotidyl transferase. The strand was fragmented into an appropriate size by ultrasonication. The ends of the fragment were blunted and SacI linkers were inserted into both ends (CCGCGAGCTCGATATCAAGCTTGTAC (SEQ ID NO:5) at the 5'-end and GGCGCTCGAGCTAT-AGTTCGAACATGGAG (SEQ ID NO:6) at the 3'-end). PCR was then performed to amplify the above cDNA fragment using the above fragment as a template and two primers (5'-GAGGTACAAGCTTGATATCGAGCTCGCGG-3 (SEQ ID NO:7) and 5'-GCCGCGAATTCTGACTAACTGAC-3' (SEQ ID NO:8)). After electro-phoresis was performed on 1.5% agarose gel, the fragment of about 400 bp was extracted from the gel and digested with EcoRI and SacI. This fragment was inserted between EcoRI and SacI sites of the expression vector pSRα-TAC II prepared as described above. The resulting cDNA library was used to transform *E. coli* JM109, and some pools, each pool being composed of 49 distinct clones, were prepared. Plasmids were prepared from each pool and introduced into COS-7 cells using LipofectAMINE. The cells were detached with 0.05% EDTA/PBS after two days. The cell surface was stained with mouse anti-IL2 receptor (Tac) IgG antibody as a first antibody and FITC-labeled goat anti-mouse IgG antibody as a second antibody. Cells expressing the Tac protein on their surfaces were screened with flow cytometer (ELITE). Tac-positive pools were further fractionated to prepare monoclones by repeating the above procedure. Consequently, three novel clones containing the signal sequence were obtained. The first is a novel gene "Entactin2" which shows high homology to entactin, a protein constructing the basement membrane protein. The second is a membrane protein that penetrates five to seven times. The third is a novel protein containing cysteine repetitive motif conserved in the TNF receptor super family (this clone is called "7F4" hereafter). Clone 7F4 is composed of only about a 400 bp fragment.

EXAMPLE 2

Cloning of Whole cDNA and Sequencing

To isolate longer fragments, the 7F4 gene was cloned again by plaque hybridization from a cDNA library of KUSA cells using the above-obtained fragment as a probe. First, the KUSA cDNA library of oligo dT priming was prepared from mRNA extracted from KUSA cells, following the ZAP-cDNA Synthesis Kit protocol (Stratagene). Phages to be used for these 50,000 KUSA cDNA library clones were spread on plates and subjected to plaque hybridization using a part of the cDNA fragment obtained by the SST method and labeled with α32P dCTP as a probe. The filter fixed with the library was incubated in hybridization buffer (50% foramide, 5× SSPE, 5× Denhardt solution, 0.1% SDS, and 0.1 mg/ml herring sperm DNA) at 42° C. for about 6 hours. The buffer was then replaced with a similar buffer but containing the probe, and the filter was further incubated at 42° C. overnight. The filter was washed in 2× SSC-0.1% SDS several times and in 0.1× SSC-0.1% SDS twice at 60° C. for 30 min to detect the label by autoradiography. The fragments obtained from the positive clones were inserted in plasmid pBluescriptII using ExAssist helper phage (Stratagene). The resulting plasmid contained a cDNA fragment of approximately 3 kbp in size comprising an initiation codon. The cDNA sequence was determined by the dye termination method (with ABI PRISM sequencing kit) using primer walking. A homology search based on the amino acid sequences deduced from the determined nucleotide sequence did not detect any genes, showing the gene coding 7F4 is novel (FIG. 1). Interestingly, clone 7F4 comprises three cysteine-rich, repetitive motifs, which are commonly conserved in the TNF super family, following the signal sequence necessary for expression on the membrane. These facts indicate that 7F4 is a novel membrane protein belonging to the TNF receptor super family (FIG. 2).

EXAMPLE 3

Northern Blotting

Figure 4:
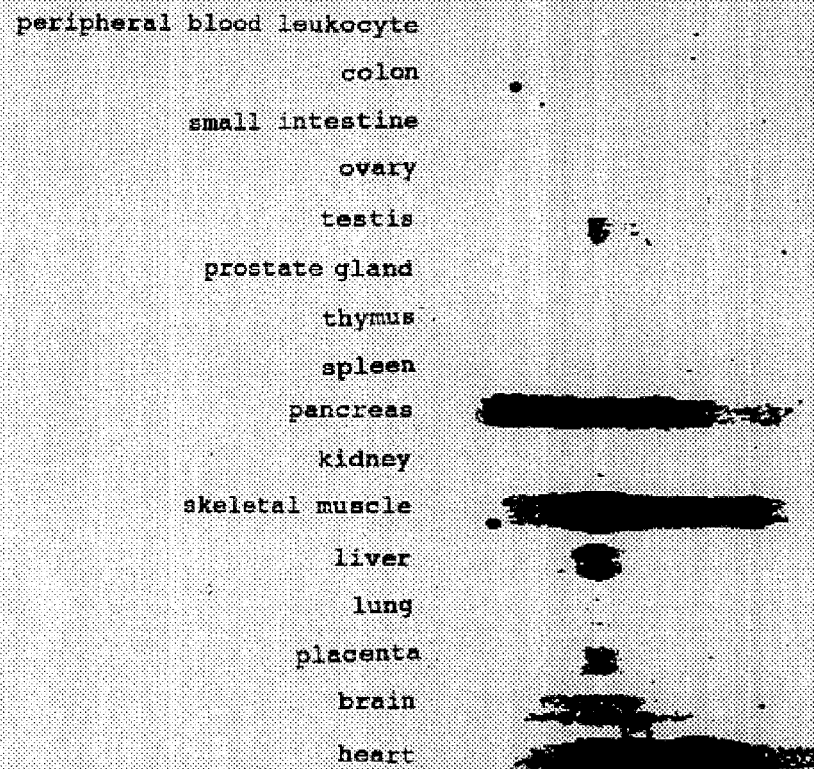
FIG. 4 shows the electrophoretic patterns of the 7F4 gene expression in various human tissues analyzed by Northern blotting.

Mouse multiple northern (MTN) blot (CLONTECH) and human MTN blot (CLONTHEH) were used as a filter for mice and humans, respectively. The regions comprising ORF of 7F4 cDNA (nucleotide number 120–480) were labeled with $\alpha^{32}P$ by multiprime labeling to be used as a probe for the hybridization. The filter for mice was incubated in ExpressHyb Hybridization Sol'n (CLONTECH) at 68° C. for approximately 2 hours, then washed in 2× SSC-0.1% SDS for several times and in 0.1× SSC-0.1% SDS twice at 60° C. The filter for humans was incubated in ExpressHyb Hybridization Sol'n (CLONTECH) at 68° C. for approximately 4 hours, and washed twice in 2× SSC-0.05% SDS at 42° C. for 10 min. The label was then detected using BAS2000 (Fuji Film). Localized expression of 7F4 was observed in all-tissues in mice (FIG. 3). In humans, 7F4 was also locally expressed, and typically, at a high level specifically in skeletal muscles and the heart (FIG. 4). The bands were detected at about 5 kb in both mice and humans, revealing that the mRNA of the gene is approximately 5 kb.

EXAMPLE 4

Expression and Preparation of GST Fusion Protein

The gene encoding the extracellular region of the 7F4 gene was amplified by PCR using, as a template, plasmid pBluescript-7F4 containing ORF of 7F4 cDNA and two primers shown in SEQ ID NO:9 and 10. The amplified gene was digested with BamHI-EcoRI and inserted at the downstream of the GST gene of pGEX-2T (Pharmacia). *E. coli* JM109 was transformed with this plasmid and incubated in the presence of 0.5 mM IPTG to induce the GST fused protein. The cells were collected after 3 hours and suspended in sonication buffer (25 mM Tris pH 8.0, 10 mM EDTA, 1 mM PMSF) containing 1 mg/ml lysozyme. The suspension was allowed to stand in ice for 30 min, ultrasonicated, then centrifuged to obtain the supernatant. The supernatant was applied onto a Glutathione Sepharose4G Column (Pharmacia) of Bulk GST purification Module (Pharmacia), and the protein was eluted and purified following the attached protocol. The protein was subjected to 10% SDS PAGE and stained with Coomassie Brilliant Blue (CBB). The protein was also detected by Western blotting using an anti GST antibody.

EXAMPLE 5

Preparation of Antiserum

Purified 7F4-GST fusion protein was added to PBS buffer to immunize rabbits. The first immunization was performed with 600 µg/head; the second and subsequent immunizations, with 200 µg/head. Immunizations were performed at intervals of 2 weeks. After the third immunization, a small amount of blood sample was collected, and the antibody titer was evaluated by ELISA. After the antibody titer was confirmed to be sufficiently high, the final immunization was performed and whole blood was collected from the heart.

EXAMPLE 6

Establishment of Cell Lines Expressing the 7F4 Gene

The full-length ORF of the 7F4-containing gene was amplified by PCR using the primers shown in SEQ ID NO:11 and SEQ ID NO:12. The amplified product was then digested with EcoRI-BamHI. The gene fragments were inserted downstream of the EF1α promoter in the expression vector pCOSI containing a neomycin gene as a drug selection marker (Sato, K., Tsuchiya, M., Saldanha, J., Koishihara, Y., Ohsugi, Y., Kishimoto, T., Bendig, M. M., (1994) Mol. Immunol. 31, 371–381, Humanization of a mouse anti-human interleukin-6 receptor antibody comparing two methods for selecting human framework regions) to construct pCOSI-7F4. After 25 μg of the plasmid was digested with PvuI, the digested products were introduced into KUSA cells (7×10$^6$ cells) by electroporation (1.6 kv, 25 uF, time const 0.36). The transformants were cultured in the medium (IMDM+10% FCS) containing 480 μg/ml of G418 for several days to select several tens of the grown clones. The cell surfaces of these clones were stained with antiserum (X 1000) and FITC-labeled anti-rabbit IgG (H+L), and analyzed with a flow cytometer (ELITE, COULTER). Some clones that expressed the 7F4 gene at a higher level than that in parental KUSA cell lines were selected.

EXAMPLE 7

Figure 5A:
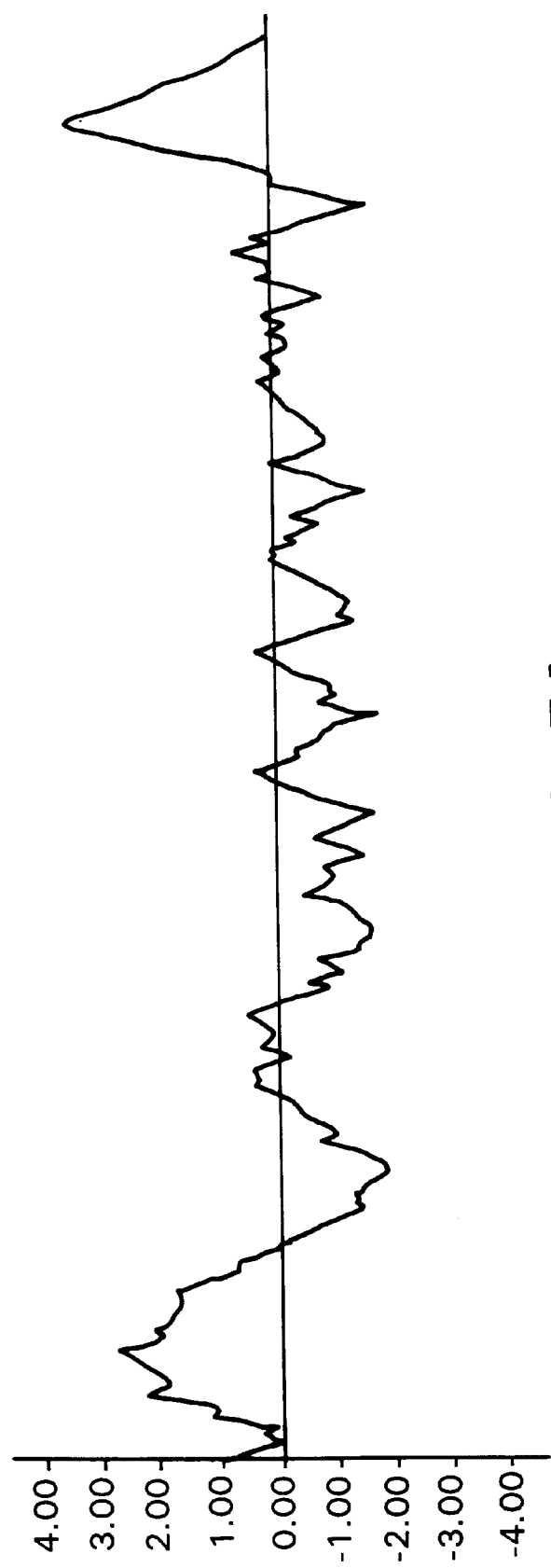
FIG. 5A shows the hydrophilicity of the 7F4 protein. The left side of the abscissa indicates the N-terminus of the 7F4 protein, and the right side shows the C-terminus. The ordinate indicates the degree of hydrophilicity.
Figure 5B:
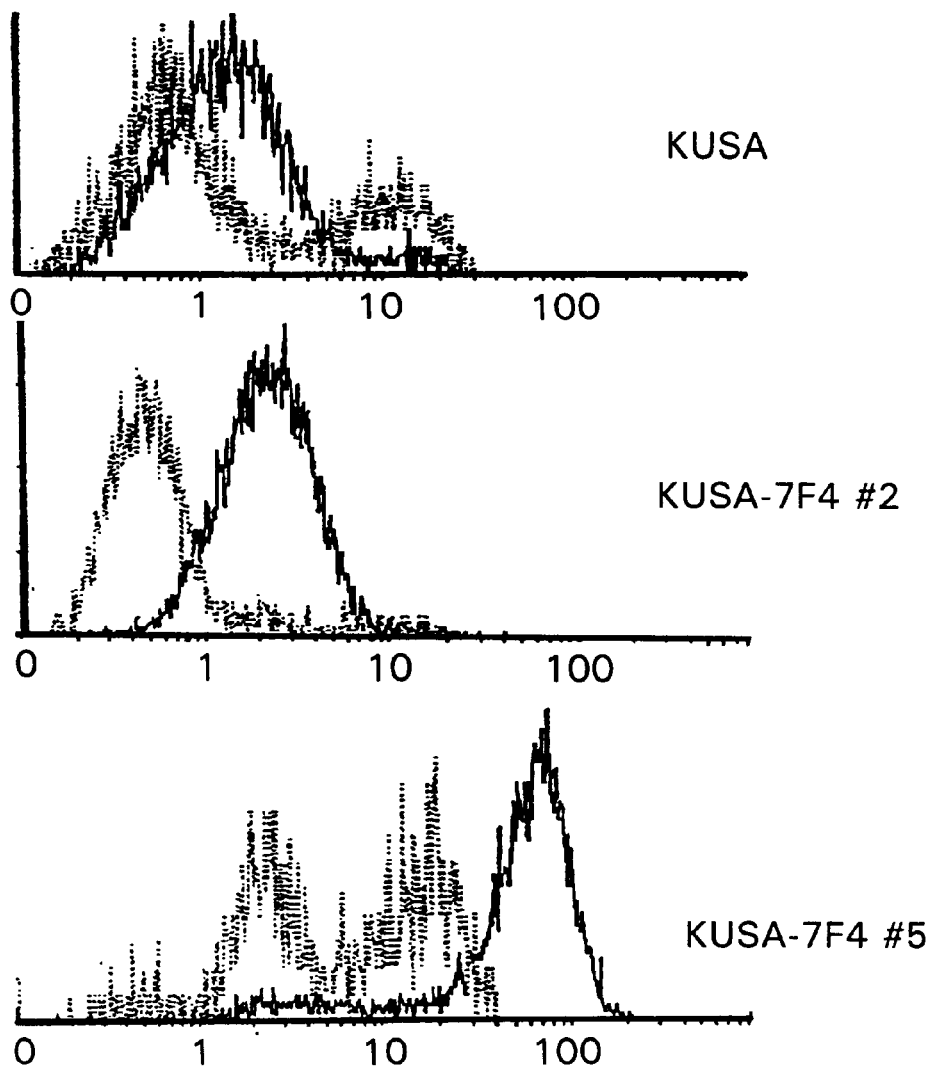
FIG. 5B shows the detected 7F4 protein on the surface of KUSA cells and the 7F4 protein on the cell surface of two clones, in which the 7F4 protein is overexpressed and treated with PI-specific phospholipase C. The dotted lines show the results in the untreated cells, and the solid lines show the results in the treated cells. The ordinate indicates the number of cells, and the abscissa shows the fluorescence intensity.

Detection of Changes in 7F4 Protein Expression on Cell Surface with Phosphatidylinositol-specific Phospholipase C Hydrophobicity analysis based on the 7F4 amino acid sequence was performed using hydrophobicity analysis software (DNASIS), and hydrophobic regions were found at the C-terminus as well as the N-terminus that contains the signal sequence. It was also found that ORF ended at the hydrophobic region at the C-terminus (FIG. 5A). This amino acid structure implies that this molecule does not comprise the intracellular region and is a protein binding to the cell membrane through a glycosyl-phosphatidylinositol (GPI) anchor (Ikezawa, H., Yamanegi, M., Taguchi, R., Miyashita, T., and Ohyabu, T. (1976) Studies on phosphatidylinositol phosphodiesterase (phospholipase C type) of *Bacillus cereus*, I. purification, properties and phophatase-releasing activity, Biochim. Biophys. Acta. 450, 154–164; Low, M. G. and Finean, J. B. (1977) Release of alkaline phosphatase from membranes by a phosphatidylinositol-specific phospholipase C, Biochem. 167, 281–284; Low, M. G. and Saltiel, A. R. (1988) Structural and functional roles of glycosyl-phosphatidylinositol in membranes, Science 239, 268–275). KUSA cell lines overexpressing 7F4 genes (KUSA-7F4#2 for low-level expression and KUSA-7F4#5 for high-level expression) were established. These KUSA cell line cells as well as the original KUSA cells were treated with phosphatidylinositol-specific phospholipase C. The 7F4 protein was stained with antiserum to analyze the quantitative change of the protein on the cell surface with a flow cytometer (ELITE). Specifically, the cells were washed with PBS and incubated in buffer (PBS+1% FCS) with or without phosphatidylinositol-specific phospholipase C (2 U/ml; Funakoshi) at 37° C. for 1 hour. The number of 7F4 protein positive cells was lowered in both cells treated with phosphatidylinositol-specific phospholipase C (FIG. 5B). This demonstrated that 7F4 molecules on the cell surface have a structure that is digestible with phosphatidylinositol-specific phospholipase C. The result indicates that the 7F4 protein is a GPI-type membrane protein expressed on the cell surface through binding of a GPI anchor to the cell surface.

EXAMPLE 8

Detection of Cell Proliferation and Differentiation by 7F4 Protein Overexpression and Detection of the Change of Alkaline Phosphatase Activity (1) Establishment of 7F4 gene-expressing Cell Lines The expression vector pCOSI-7F4 (25 μg) in which the 7F4 gene is controlled by the EF1α promoter was digested with PvuI, and the digested products were introduced into KUSA (7×10$^6$ cells) or CHO cells by electroporation (1.6 kv, 25 uF, time const 0.36). The cells were cultured for several days in a medium (IMDM+10% FCS or α-MEM+10% FCS) containing 480 μg/ml of G418. Several tens of developed clones were collected. The cell surfaces of these clones were stained with 7F4 antiserum (X 1000) and FITC-labeled anti-rabbit IgG (H+L) then analyzed with a flow cytometer (ELITE). Some clones in which the expression of 7F4 was higher than that in parental KUSA or CHO cells were selected. Transformant #2, in which pCOSI-7F4 was introduced and which weakly expressed the 7F4 protein, and transformant #11, in which pCOSI-7F4 was introduced and which strongly expressed the protein, were obtained. The morphology of these transformants was markedly changed after the continued culture. Parental KUSA cells are characterized by the oval and fibroblast-like form. In contrast, transformants expanded and contained more projections.

(2) Proliferation Analysis

Figure 6:
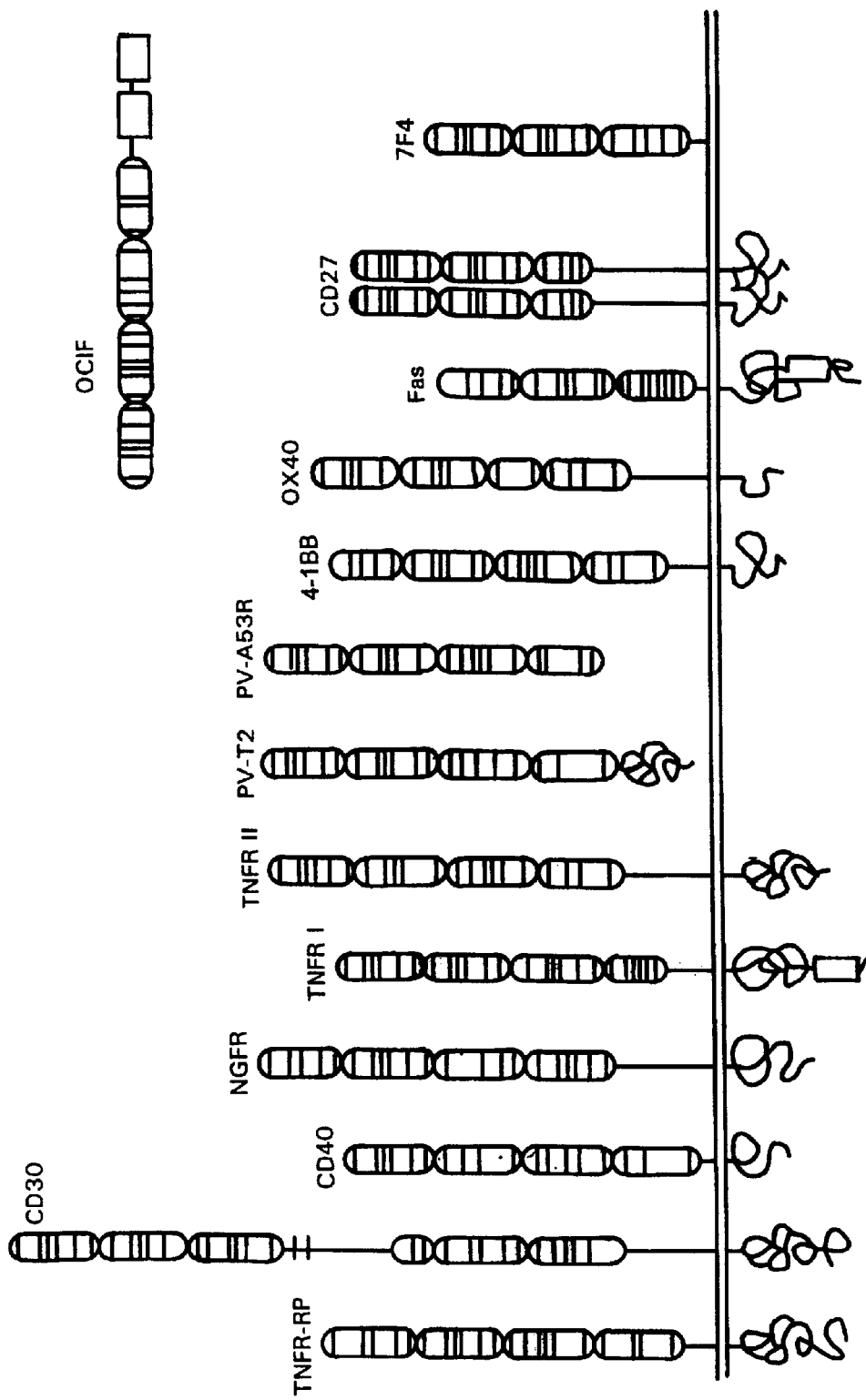
FIG. 6 shows the structure of molecules belonging to the TNF receptor super family. The cysteine-rich, repetitive sequences are circled by ovals. Horizontal lines in the ovals indicate the location of the cysteine residues.

5×10$^3$ KUSA cells and 1×10$^3$ CHO cells were cultured in each well of a 12-well plate. The cells were detached from the plate in the course of time and counted. The expression level of exogenous 7F4 was the highest in transformant #11, moderate in #8 and #5, and the lowest in #2. The proliferation rate of these transformants was lowered in correlation with the expression level of exogenous 7F4, compared to the parental cells (FIG. 6). These results revealed that high-level expression of 7F4 genes in KUSA cells induced the osteoblast form of the cells.

(3) Alkaline Phosphatase Activity Assay

Figure 7:
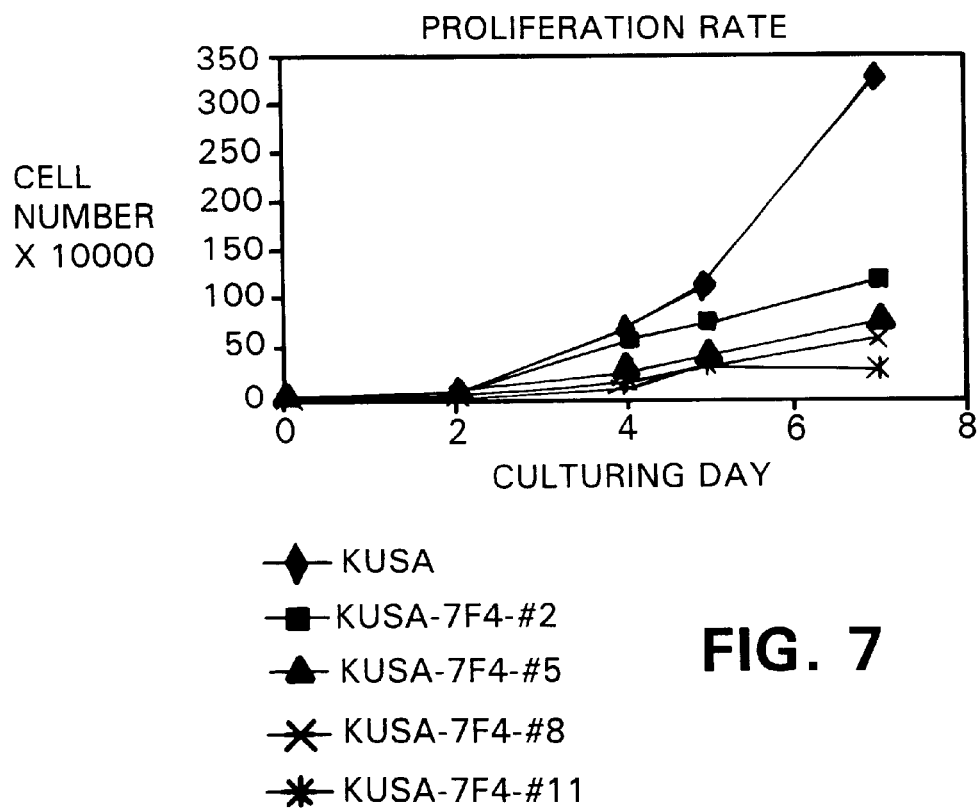
FIG. 7 shows proliferation inhibition of KUSA cells by overexpression of the 7F4 gene. The proliferation rate of KUSA cells in which 7F4 genes were overexpressed was measured by counting the number of cells with the passage of time.

The cells were cultured in six wells, washed twice in PBS, and detached in 700 μl of sonication buffer (50 mM Tris (pH 7.2), 0.1% Triton X-100). The cells were lightly disintegrated by ultrasonication and centrifuged at 15,000 rpm for 15 min. The protein concentration was measured by a protein assay kit (Bio-Rad). Incubation buffer (0.1 M 2-amino-2-methyl-1-propanol/HCl (pH 10.5), 2 mM MgCl$_2$) containing 20 mM p-nitrophenolphosphate as a substrate was added to 2 to 20 μg of the cell lysate in an equivalent amount, and the mixture was incubated at 37° C. for 30 min. After NaOH was added to 0.1 N to stop the reaction, the produced p-nitrophenol was colorimetrically determined at OD405. Parental KUSA and transformants #2 and #11 were cultured and, when the cells became about 80% confluent, namely at the proliferation stage, cell lysate was prepared to determine intracellular alkaline phosphatase activity, which is a marker for differentiation of osteoblasts. As a result, the alkaline phosphatase activity was increased in correlation with the expression level of exogenous 7F4 (FIG. 7).

Figure 8:
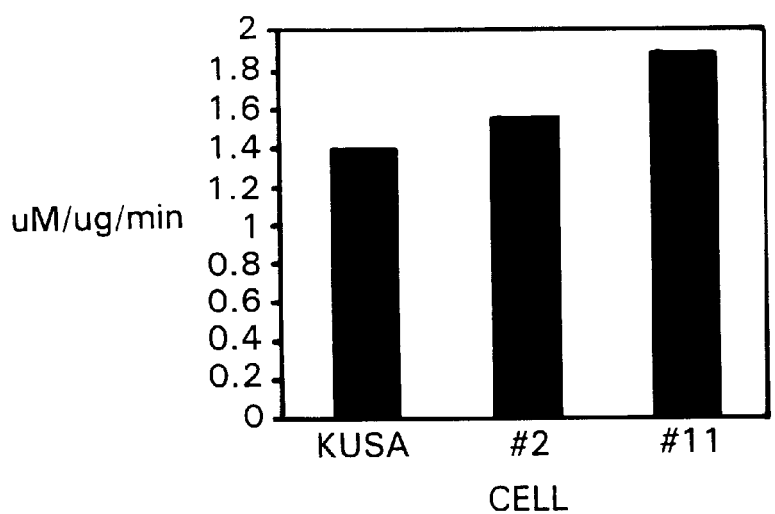
FIG. 8 shows the detected changes of alkaline phosphatase activity by the expression of 7F4 genes. Cell lysate was prepared from KUSA cell transformants that overexpressed the 7F4 gene before the cells become confluent, and intracellular alkaline phosphatase activity was measured.
Figure 9:
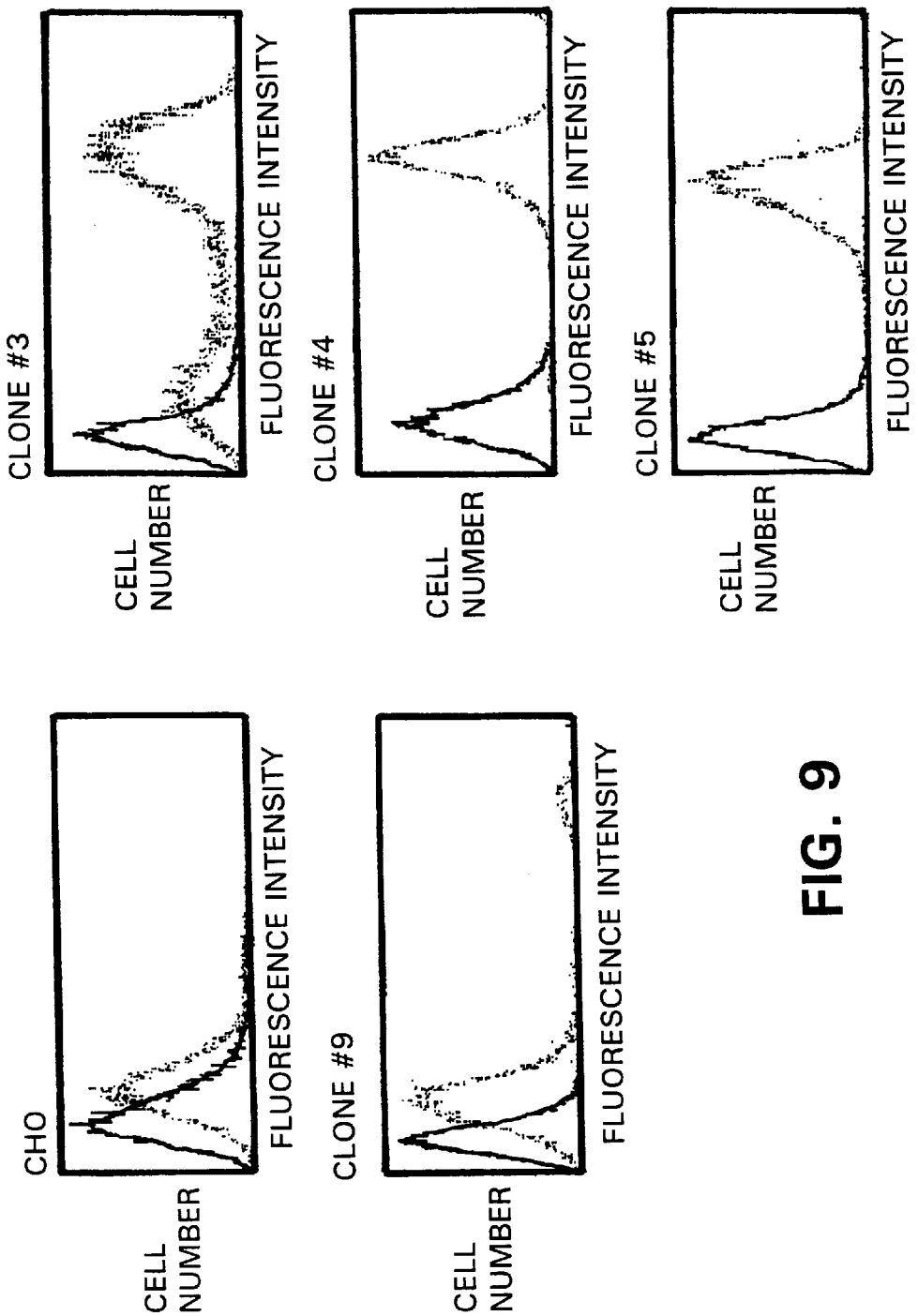
FIG. 9 shows the detected expression of 7F4 genes in CHO cells and transformants in which 7F4 genes were introduced. Clones obtained by transforming CHO cells with the 7F4 expression vector were stained with the 7F4 antiserum, and the expression level was analyzed by ELITE.
Figure 10:
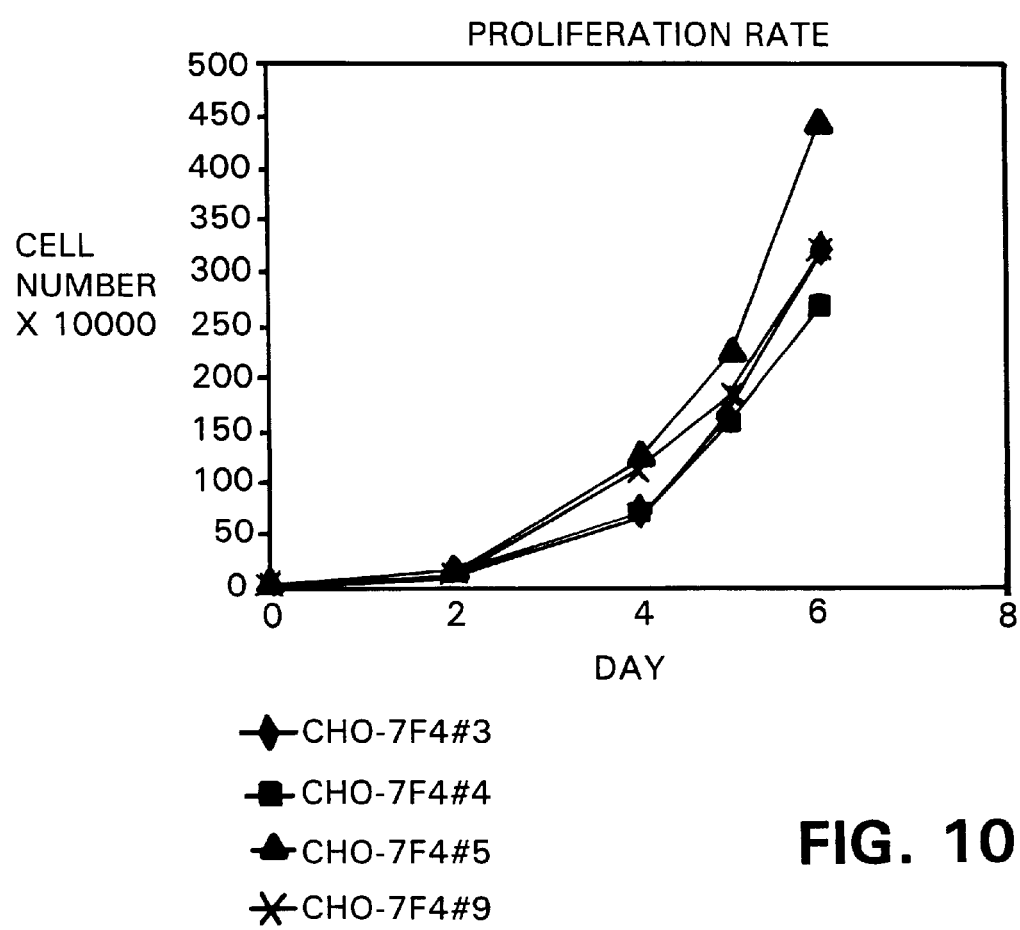
FIG. 10 shows the detected change of the proliferation rate of COS cells which expressed 7F4 genes. The proliferation rate of COS cells which overexpressed 7F4 genes was measured by counting the number of cells with the passage of time.

The same experiment was conducted using CHO cells. Similar to KUSA cells, pCOSI-7F4 was introduced into CHO cells, and several cell lines which overexpressed exogenous 7F4 were established (FIG. 8). The effects of overexpression of 7F4 on the proliferation rate of transformants were analyzed. Contrary to expectations, high expression of the 7F4 gene did not affect proliferation of CHO cells at all (FIG. 9). No change of cell morphology was observed.

INDUSTRIAL APPLICABILITY

The present invention provides a novel secretory membrane protein which belongs to the TNF super family and is thought to be involved in differentiation or the like phenomena of osteoblasts, a gene encoding said protein, a vector into which said gene has been introduced, a host cell carrying said vector, and an antibody against said protein. The invention also provides a method for screening a drug candidate using said protein. The proteins, genes, and antibodies of the present invention and the compounds isolated by the screening method of the invention can be used as medicines. The number of patients suffering from bone disorders, such as osteoporosis, is predicted to increase with the aging of society. The proteins of the invention would be involved in differentiation and activation of osteoblasts, which are important for bone formation. The proteins of the present invention, the antibodies, and ligands against the proteins can thus contribute to treating bone disorders and to clarifying the mechanism of bone formation.

What is claimed is:

1. A substantially pure polypeptide comprising an amino acid sequence at least 90% identical to SEQ ID NO:2, wherein the polypeptide induces differentiation of an osteoblast.

2. The polypeptide of claim 1, wherein the amino acid sequence is at least 95% identical to SEQ ID NO:2.

3. The polypeptide of claim 1, wherein the amino acid sequence is at least 99% identical to SEQ ID NO:2.

4. A method of screening for a compound that binds to a polypeptide, the method comprising:
   providing the polypeptide of claim 1;
   contacting a test compound with the polypeptide; and
   determining whether the test compound has bound to the polypeptide.

5. A method of screening for a compound that induces osteoblast differentiation, the method comprising:
   culturing osteoblasts;
   providing the polypeptide of claim 1 to said osteoblasts;
   contacting a test compound with the polypeptide;
   measuring osteoblast differentiation; and selecting a test compound that increases the ability of the polypeptide to induce differentiation compared to the ability of the polypeptide to induce differentiation in the absence of the test compound.

6. A method of screening for a compound that inhibits osteoblast differentiation, the method comprising:
   culturing osteoblasts;
   providing the polypeptide of claim 1 to said osteoblasts;
   contacting a test compound with the polypeptide;
   measuring osteoblast differentiation; and
   selecting a test compound that reduces the ability of the polypeptide to induce differentiation compared to the ability of to polypeptide to induce differentiation in the absence of the test compound.

7. A substantially pure polypeptide comprising SEQ ID NO:2.

8. A method of screening for a compound that binds to a polypeptide, the method comprising:
   providing the polypeptide of claim 7;
   contacting a test compound with the polypeptide; and determining whether the test compound has bound to the polypeptide.

9. A method of screening for a compound that induces osteoblast differentiation, the method comprising:
   culturing osteoblasts;
   providing the polypeptide of claim 7 to said osteoblasts;
   contacting a test compound with the polypeptide;
   measuring osteoblast differentiation; and
   selecting a test compound that increases the ability of the polypeptide to induce differentiation compared to the ability of the polypeptide to induce differentiation in the absence of the test compound.

10. A method of screening for a compound that inhibits osteoblast differentiation, the method comprising:
    culturing osteoblasts;
    providing the polypeptide of claim 7 to said osteoblasts;
    contacting a test compound with the polypeptide;
    measuring osteoblast differentiation; and
    selecting a test compound that reduces the ability of the polypeptide to induce differentiation compared to the ability of the polypeptide to induce differentiation in the absence of the test compound.

11. A substantially pure polypeptide comprising SEQ ID NO:1.

12. A method of screening for a compound that binds to a polypeptide, the method comprising:
    providing the polypeptide of claim 11;
    contacting a test compound with the polypeptide; and
    determining whether the test compound has bound to the polypeptide.

13. A method of screening for a compound that induces osteoblast differentiation, the method comprising:
    culturing osteoblasts;
    providing the polypeptide of claim 11 to said osteoblasts;
    contacting a test compound with the polypeptide;
    measuring osteoblast differentiation; and
    selecting a test compound that increases the ability of the polypeptide to induce differentiation compared to the ability of the polypeptide to induce differentiation in the absence of the test compound.

14. A method of screening for a compound that inhibits osteoblast differentiation, the method comprising:
    culturing osteoblasts;
    providing the polypeptide of claim 11 to said osteoblasts;
    contacting a test compound with the polypeptide;
    measuring osteoblast differentiation; and
    selecting a test compound that reduces the ability of the polypeptide to induce differentiation compared to the ability of the polypeptide to induce differentiation in the absence of the test compound.

15. A substantially pure polypeptide comprising the amino acid sequence of SEQ ID NO:2 containing up to 30 conservative amino acid substitutions, wherein the polypeptide induces differentiation of an osteoblast.

16. The polypeptide of claim 15, wherein the amino acid sequence contains up to 15 conservative amino acid substitutions.

17. The polypeptide of claim 15, wherein the amino acid sequence contains up to 5 conservative amino acid substitutions.

18. The polypeptide of claim 15, wherein the amino acid sequence contains up to 3 conservative amino acid substitutions.

19. A method of screening for a compound that binds to a polypeptide, the method comprising:
  providing the polypeptide of claim 15;
  contacting a test compound with the polypeptide; and determining whether the test compound has bound to the polypeptide.

20. A method of screening for a compound that induces osteoblast differentiation, the method comprising:
  culturing osteoblasts;
  providing to polypeptide of claim 15 to said osteoblasts;
  contacting a test compound with to polypeptide;
  measuring osteoblast differentiation; and
  selecting a test compound that increases the ability of the polypeptide to induce differentiation compared to the ability of the polypeptide to induce differentiation in the absence of the test compound.

21. A method of screening for a compound that inhibits osteoblast differentiation, the method comprising;
  culturing osteoblasts;
  providing the polypeptide of claim 15 to said osteoblasts;
  contacting a test compound with the polypeptide;
  measuring osteoblast differentiation; and
  selecting a test compound that reduces the ability of the polypeptide to induce differentiation compared to the ability of the polypeptide to induce differentiation in the absence of the test compound.

22. A substantially pure polypeptide encoded by a first nucleic acid that hybridizes under stringent conditions (0.2× SSC and 0.1% SDS at 68° C.) to a second nucleic acid consisting of SEQ ID NO:3, wherein the polypeptide induces differentiation of an osteoblast.

23. A method of screening for a compound that binds to a polypeptide, the method comprising:
  providing the polypeptide of claim 22;
  contacting a test compound with the polypeptide; and determining whether the test compound has bound to the polypeptide.

24. A method of screening for a compound that induces osteoblast differentiation, the method comprising:
  culturing osteoblasts;
  providing the polypeptide of claim 22 to said osteoblasts;
  contacting a test compound with the polypeptide;
  measuring osteoblast differentiation; and
  selecting a test compound that increases the ability of the polypeptide to induce differentiation compared to the ability of the polypeptide to induce differentiation in the absence of to test compound.

25. A method of screening for a compound that inhibits osteoblast differentiation, the method comprising:
  culturing osteoblasts;
  providing the polypeptide of claim 22 to said osteoblasts;
  contacting a test compound with the polypeptide;
  measuring osteoblast differentiation; and
  selecting a test compound that reduces the ability of the polypeptide to induce differentiation compared to the ability of the polypeptide to induce differentiation in the absence of the test compound.

26. A substantially pure polypeptide consisting of the sequence of SEQ ID NO:1.

27. A substantially pure polypeptide consisting of the sequence of SEQ ID NO:2.

* * * * *

SEQUENCE LISTING

<160> NUMBER OF SEQ ID NOS: 13

<210> SEQ ID NO 1
<211> LENGTH: 176
<212> TYPE: PRT
<213> ORGANISM: Mus musculus

<400> SEQUENCE: 1

```
Met Val Thr Phe Ser His Val Ser Ser Leu Ser His Trp Phe Leu Leu
 1               5                  10                  15

Leu Leu Leu Leu Asn Leu Phe Leu Pro Val Ile Phe Ala Met Pro Glu
            20                  25                  30

Ser Tyr Ser Phe Asn Cys Pro Asp Gly Glu Tyr Gln Ser Asn Asp Val
        35                  40                  45

Cys Cys Lys Thr Cys Pro Ser Gly Thr Phe Val Lys Ala Pro Cys Lys
    50                  55                  60

Ile Pro His Thr Gln Gly Gln Cys Glu Lys Cys His Pro Gly Thr Phe
65                  70                  75                  80

Thr Gly Lys Asp Asn Gly Leu His Asp Cys Glu Leu Cys Ser Thr Cys
                85                  90                  95

Asp Lys Asp Gln Asn Met Val Ala Asp Cys Ser Ala Thr Ser Asp Arg
           100                 105                 110

Lys Cys Glu Cys Gln Ile Gly Leu Tyr Tyr Tyr Asp Pro Lys Phe Pro
       115                 120                 125

Glu Ser Cys Arg Pro Cys Thr Lys Cys Pro Gln Gly Ile Pro Val Leu
   130                 135                 140

Gln Glu Cys Asn Ser Thr Ala Asn Thr Val Cys Ser Ser Ser Val Ser
145                 150                 155                 160

Asn Pro Arg Asn Trp Leu Phe Leu Leu Met Leu Ile Val Phe Cys Ile
                165                 170                 175
```

<210> SEQ ID NO 2
<211> LENGTH: 148
<212> TYPE: PRT
<213> ORGANISM: Mus musculus

<400> SEQUENCE: 2

```
Ala Met Pro Glu Ser Tyr Ser Phe Asn Cys Pro Asp Gly Glu Tyr Gln
 1               5                  10                  15

Ser Asn Asp Val Cys Cys Lys Thr Cys Pro Ser Gly Thr Phe Val Lys
            20                  25                  30

Ala Pro Cys Lys Ile Pro His Thr Gln Gly Gln Cys Glu Lys Cys His
        35                  40                  45

Pro Gly Thr Phe Thr Gly Lys Asp Asn Gly Leu His Asp Cys Glu Leu
    50                  55                  60

Cys Ser Thr Cys Asp Lys Asp Gln Asn Met Val Ala Asp Cys Ser Ala
```

```
              65                  70                  75                  80
Thr Ser Asp Arg Lys Cys Glu Cys Gln Ile Gly Leu Tyr Tyr Tyr Asp
                    85                  90                  95

Pro Lys Phe Pro Glu Ser Cys Arg Pro Cys Thr Lys Cys Pro Gln Gly
                100                 105                 110

Ile Pro Val Leu Gln Glu Cys Asn Ser Thr Ala Asn Thr Val Cys Ser
            115                 120                 125

Ser Ser Val Ser Asn Pro Arg Asn Trp Leu Phe Leu Met Leu Ile
    130                 135                 140

Val Phe Cys Ile
145

<210> SEQ ID NO 3
<211> LENGTH: 1509
<212> TYPE: DNA
<213> ORGANISM: Mus musculus
<220> FEATURE:
<221> NAME/KEY: CDS
<222> LOCATION: (12)...(539)

<400> SEQUENCE: 3
agctcacagc c atg gtt acc ttc agc cac gtc tcc agt ctg agt cac tgg         50
             Met Val Thr Phe Ser His Val Ser Ser Leu Ser His Trp
               1               5                  10 ttc ctc ttg ctg ctg ctg aat ctg ttc ttg ccg gta ata ttt gct              98
Phe Leu Leu Leu Leu Leu Asn Leu Phe Leu Pro Val Ile Phe Ala
         15                  20                  25 atg cct gaa tca tac tcc ttc aac tgt ccc gat ggt gaa tac cag tct         146
Met Pro Glu Ser Tyr Ser Phe Asn Cys Pro Asp Gly Glu Tyr Gln Ser
    30                  35                  40                  45 aat gat gtc tgt tgc aag acc tgt ccc tca ggt aca ttt gtc aag gcg         194
Asn Asp Val Cys Cys Lys Thr Cys Pro Ser Gly Thr Phe Val Lys Ala
                50                  55                  60 ccc tgc aaa atc ccc cat act caa gga caa tgt gag aag tgt cac cca         242
Pro Cys Lys Ile Pro His Thr Gln Gly Gln Cys Glu Lys Cys His Pro
            65                  70                  75 gga aca ttc aca ggg aaa gat aat ggc ctg cat gat tgt gaa ctt tgc         290
Gly Thr Phe Thr Gly Lys Asp Asn Gly Leu His Asp Cys Glu Leu Cys
        80                  85                  90 tcc acc tgt gat aaa gac cag aat atg gtg gct gac tgt tct gcc acc         338
Ser Thr Cys Asp Lys Asp Gln Asn Met Val Ala Asp Cys Ser Ala Thr
    95                 100                 105 agt gac cgg aaa tgc gag tgc caa ata ggt ctt tac tac tat gac cca         386
Ser Asp Arg Lys Cys Glu Cys Gln Ile Gly Leu Tyr Tyr Tyr Asp Pro
110                 115                 120                 125 aaa ttt ccg gaa tca tgc cgc cca tgt acc aag tgt ccc caa gga atc         434
Lys Phe Pro Glu Ser Cys Arg Pro Cys Thr Lys Cys Pro Gln Gly Ile
                130                 135                 140 cct gtc ctc cag gaa tgc aac tcc aca gct aac act gtg tgc agt tca         482
Pro Val Leu Gln Glu Cys Asn Ser Thr Ala Asn Thr Val Cys Ser Ser
            145                 150                 155 tct gtt tca aat ccc aga aac tgg ctg ttc cta ctg atg cta att gtc         530
Ser Val Ser Asn Pro Arg Asn Trp Leu Phe Leu Leu Met Leu Ile Val
        160                 165                 170 ttc tgt atc tgaagaagat aaaggttcta cagatggtgt ctgtagcttc                 579
Phe Cys Ile
        175 cttttattgc tgtgaagaga aaccatggag gcaactcttt catttatttt tattttttaa       639 tgtcttgaac ttgatttgaa gaccaggctg gactcaaact cacagagatc cggactaggc       699
```

```
acctctaata taggaaaaca ttgaattggg actggcttac agtttcagaa gttctgtcca    759
tgattatcat agtgcgaagc atggaggcac ggaggcacac atggtgctgg agaagaagct    819
gagagttctg catcttgatc tgcaagcaat aaaaggagag tgtgtgccac actacacata    879
gcttgaacat aggagacctc aaagcctgtc cccacagtga caaacttcct ccaacaaggt    939
catacctcct aataatacca tttcttatga ggcaagcatt caaacacatg agtctatgag    999
ggccaaacca attcaaacca ccacaggtta acaattgccc tctgcagctc tctggtggag   1059
gccctccttg agagtaagta acaatttaga tgaaggcaag tcctggtatc aggtccaaaa   1119
gaaactcagg atgaatggtc cactgtggtt cctattaaca tactgaagaa catgacctca   1179
ccttagactt ctccacctca ctggcttccc ttcccctagc ttctcattcc caggtaaccc   1239
tgccattttt tggtaatgtg ccttcttggt tcttcctctc ctttccccct ctcttctggt   1299
ccttatttct cttcctctcc cactctccac cagccgcctc ttaaggcctg agtcagtctg   1359
caggccatgt ttaatctact actttctctc tgctctggac tcatccagat gtctctggct   1419
gagctctccc tcctatctac aataaaacct tcccctaac cagaaatgga acagttttgt   1479
cctcactttg tacatctggt gcctgaaacc                                    1509

<210> SEQ ID NO 4
<211> LENGTH: 43
<212> TYPE: DNA
<213> ORGANISM: Artificial Sequence
<220> FEATURE:
<223> OTHER INFORMATION: Synthetically generated primer

<400> SEQUENCE: 4
gcggccgcga attctgacta actgacgggg ggggggggg ggg                       43

<210> SEQ ID NO 5
<211> LENGTH: 26
<212> TYPE: DNA
<213> ORGANISM: Artificial Sequence
<220> FEATURE:
<223> OTHER INFORMATION: Synthetically generated primer

<400> SEQUENCE: 5
ccgcgagctc gatatcaagc ttgtac                                         26

<210> SEQ ID NO 6
<211> LENGTH: 29
<212> TYPE: DNA
<213> ORGANISM: Artificial Sequence
<220> FEATURE:
<223> OTHER INFORMATION: Synthetically generated primer

<400> SEQUENCE: 6
ggcgctcgag ctatagttcg aacatggag                                      29

<210> SEQ ID NO 7
<211> LENGTH: 29
<212> TYPE: DNA
<213> ORGANISM: Artificial Sequence
<220> FEATURE:
<223> OTHER INFORMATION: Synthetically generated primer

<400> SEQUENCE: 7
gaggtacaag cttgatatcg agctcgcgg                                      29

<210> SEQ ID NO 8
```

-continued

<210> SEQ ID NO 8
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 8
gccgcgaatt ctgactaact gac                                              23

<210> SEQ ID NO 9
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 9
ggatccttca actgtcccga tggt                                             24

<210> SEQ ID NO 10
<211> LENGTH: 26
<212> TYPE: DNA
<213> ORGANISM: Artificial Sequence
<220> FEATURE:
<223> OTHER INFORMATION: Synthetically generated primer

<400> SEQUENCE: 10
gaattccaca cagtgttagc tgtgga                                           26

<210> SEQ ID NO 11
<211> LENGTH: 36
<212> TYPE: DNA
<213> ORGANISM: Artificial Sequence
<220> FEATURE:
<223> OTHER INFORMATION: Synthetically generated primer

<400> SEQUENCE: 11
ccgaattcca ccatggttac cttcagccac gtctcc                                36

<210> SEQ ID NO 12
<211> LENGTH: 35
<212> TYPE: DNA
<213> ORGANISM: Artificial Sequence
<220> FEATURE:
<223> OTHER INFORMATION: Synthetically generated primer

<400> SEQUENCE: 12
ccggatcctc agatacagaa gacaattagc atcag                                 35

<210> SEQ ID NO 13
<211> LENGTH: 123
<212> TYPE: PRT
<213> ORGANISM: Mus musculus

<400> SEQUENCE: 13

Cys Pro Gly Gly Lys Tyr Val His Ser Lys Asn Asn Ser Ile Cys Cys
 1               5                  10                  15

Thr Lys Cys His Lys Gly Thr Tyr Leu Val Ser Asp Cys Pro Ser Pro
            20                  25                  30

Gly Arg Asp Thr Val Cys Arg Glu Cys Glu Lys Gly Thr Phe Thr Ala
        35                  40                  45

Ser Gln Asn Tyr Leu Arg Gln Cys Leu Ser Cys Lys Thr Cys Arg Lys
    50                  55                  60

Glu Met Ser Gln Val Glu Ile Ser Pro Cys Gln Ala Asp Lys Asp Thr

-continued

```
                65                  70                  75                  80
Val Cys Gly Cys Lys Glu Asn Gln Phe Gln Arg Tyr Leu Ser Glu Thr
                85                  90                  95
His Phe Gln Cys Val Asp Cys Ser Pro Cys Phe Asn Gly Thr Val Thr
               100                 105                 110
Ile Pro Cys Lys Glu Thr Gln Asn Thr Val Cys
               115                 120
```